United States Patent [19]

Agrawal et al.

[11] Patent Number: 5,626,847

[45] Date of Patent: May 6, 1997

[54] METHOD OF PURIFYING CYCLITOLS

[76] Inventors: Pramod Agrawal, 5007 Birchwood Rd., Santa Barbara, Calif. 93111; Israel Rabinowitz, 2534 Foothill Rd., Santa Barbara, Calif. 93105

[21] Appl. No.: 634,089

[22] Filed: Dec. 20, 1990

[51] Int. Cl.$^6$ ................................................ A61K 35/78
[52] U.S. Cl. ........................................................ 424/195.1
[58] Field of Search ................................ 435/100, 105, 435/171; 424/195.1

[56] References Cited

U.S. PATENT DOCUMENTS

| | | | |
|---|---|---|---|
| 4,356,262 | 10/1982 | Heady | 435/97 |
| 5,064,762 | 11/1991 | Rabinowitz | 435/155 |

FOREIGN PATENT DOCUMENTS

| | | | |
|---|---|---|---|
| 13353 | 5/1928 | Australia | 435/100 |
| 2-261387 | 10/1990 | Japan . | |
| 10445 | of 1910 | United Kingdom | 435/100 |

OTHER PUBLICATIONS

Greenberg M.L. Regulatory Mutations of Inositol Biosynthesis in Yeast: . . . , Genetics 100 19–33, 1982.
Reed, Gerald, Prescott & Donn's Industrial Microbiology 4th Ed AVI Pub, Westport CT 1982, pp. 436–437.
Demain, Arnold, Biology of Industrial Microorganisms 1985, Benjamin/Cummings Pub Co. Calif. 517–21.

*Primary Examiner*—Ralph J. Gitomer
*Attorney, Agent, or Firm*—Donald D. Mon

[57] ABSTRACT

A method of purifying cyclitols, particularly inositol, from mixtures including simple and complex carbohydrates begins by reducing the concentration of carbohydrates other than cyclitols to facilitate separation and crystallization of the cyclitol in high purity. Other carbohydrates can be removed or depleted from a mixture by adding a microorganism to the mixture which preferentially consumes carbohydrates but not cyclitol.

11 Claims, 3 Drawing Sheets

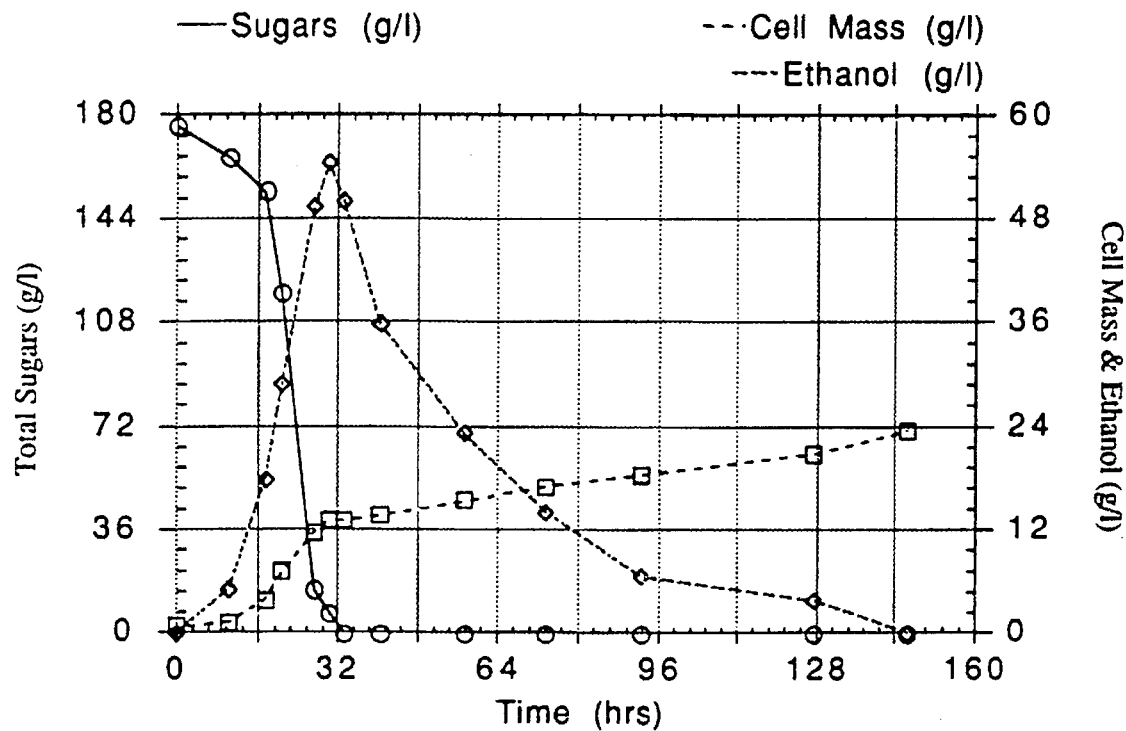
Figure 1A – Treatment of 30° B AHJ with DD2
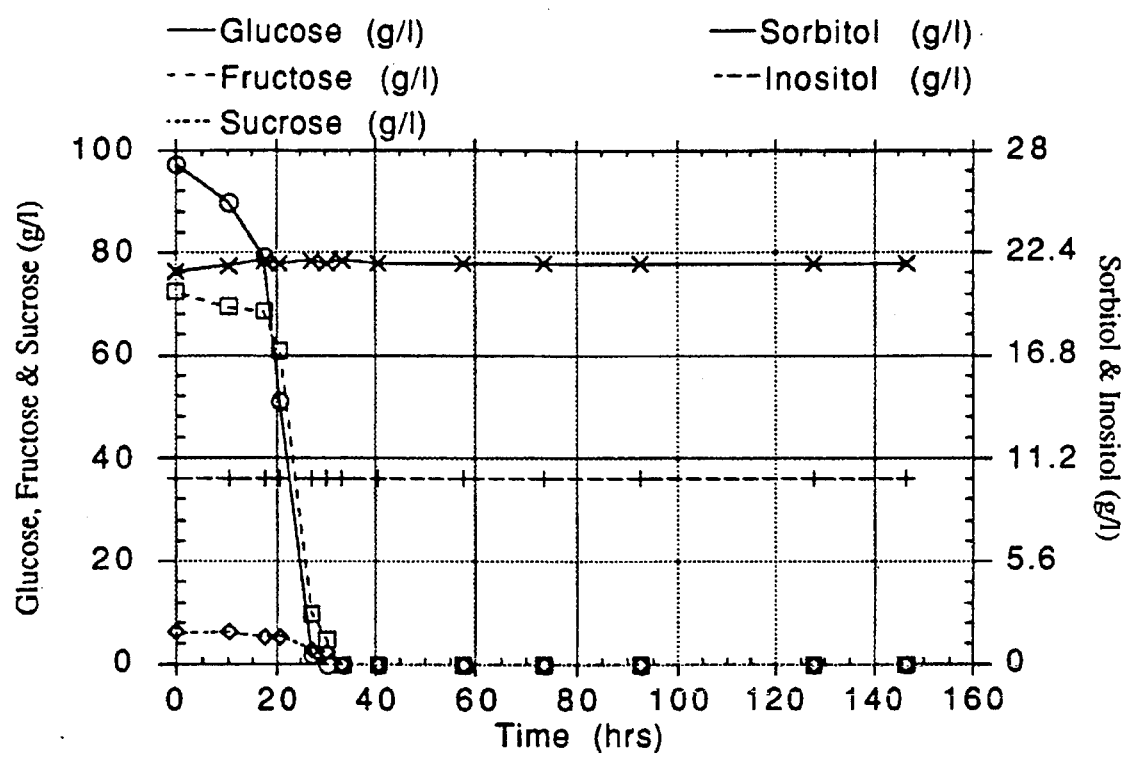
Figure 1B – Treatment of 30° B AHJ with DD2

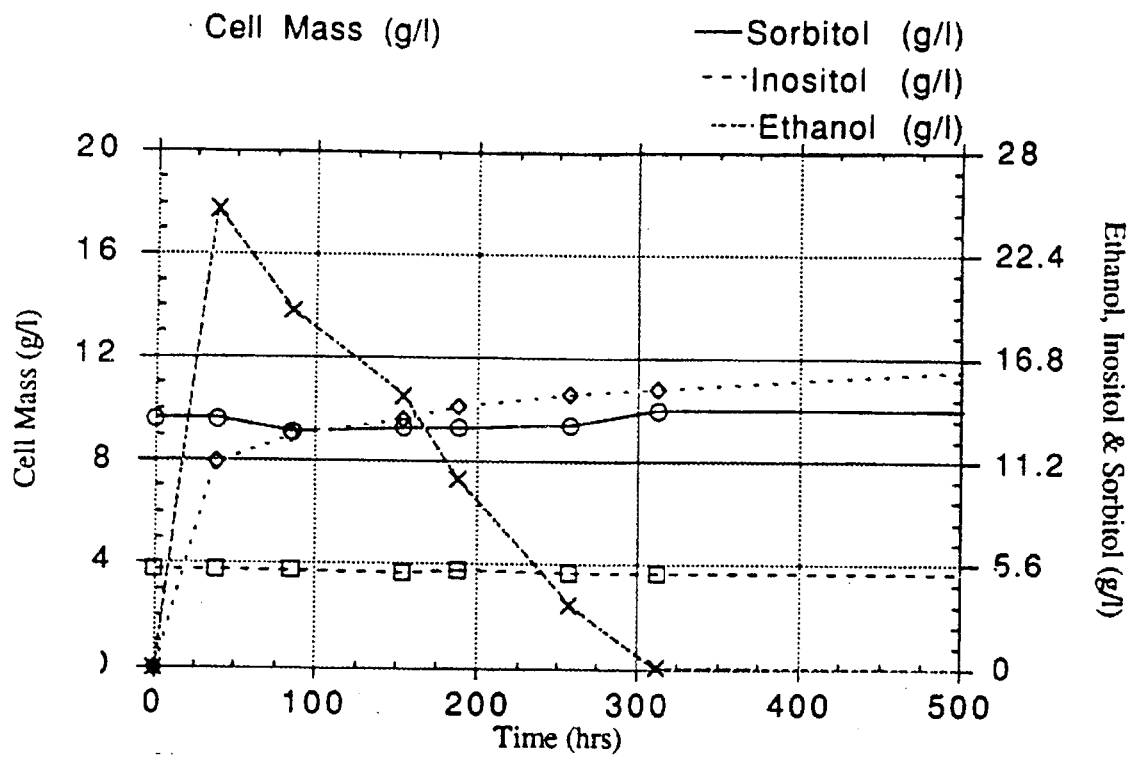
Figure 2A – Treatment of Unmodified 12° B AHJ with DD2
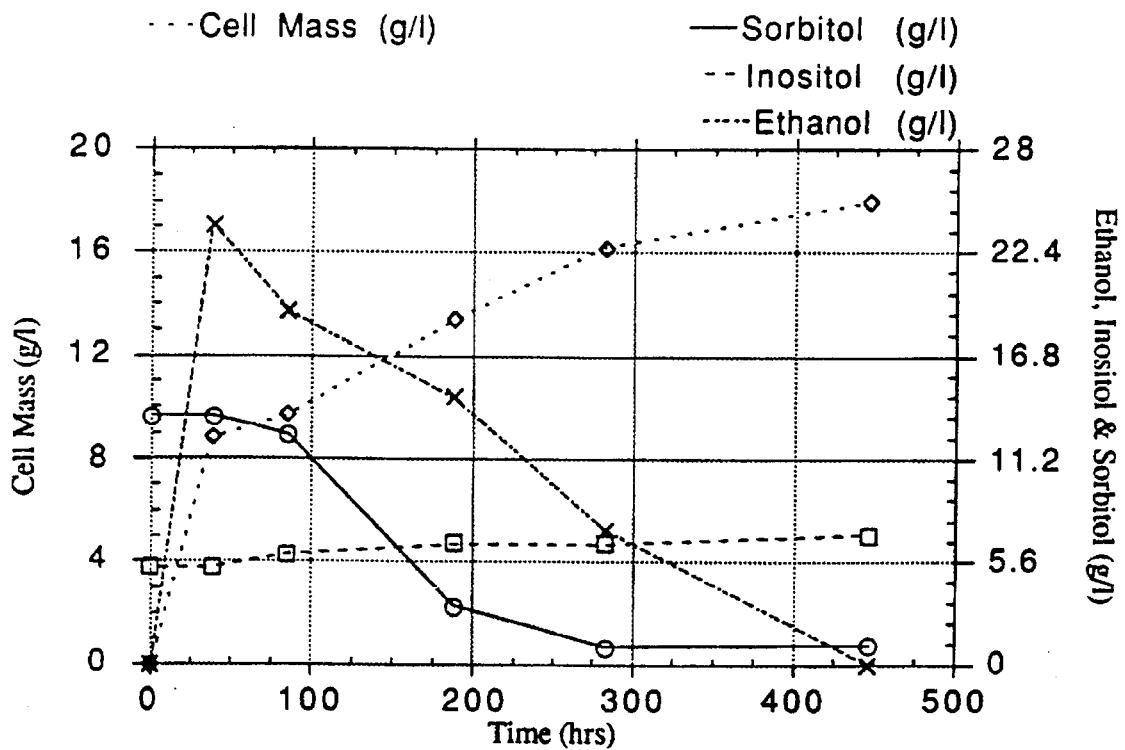
Figure 2B – Treatment of Modified 12° B AHJ with DD2

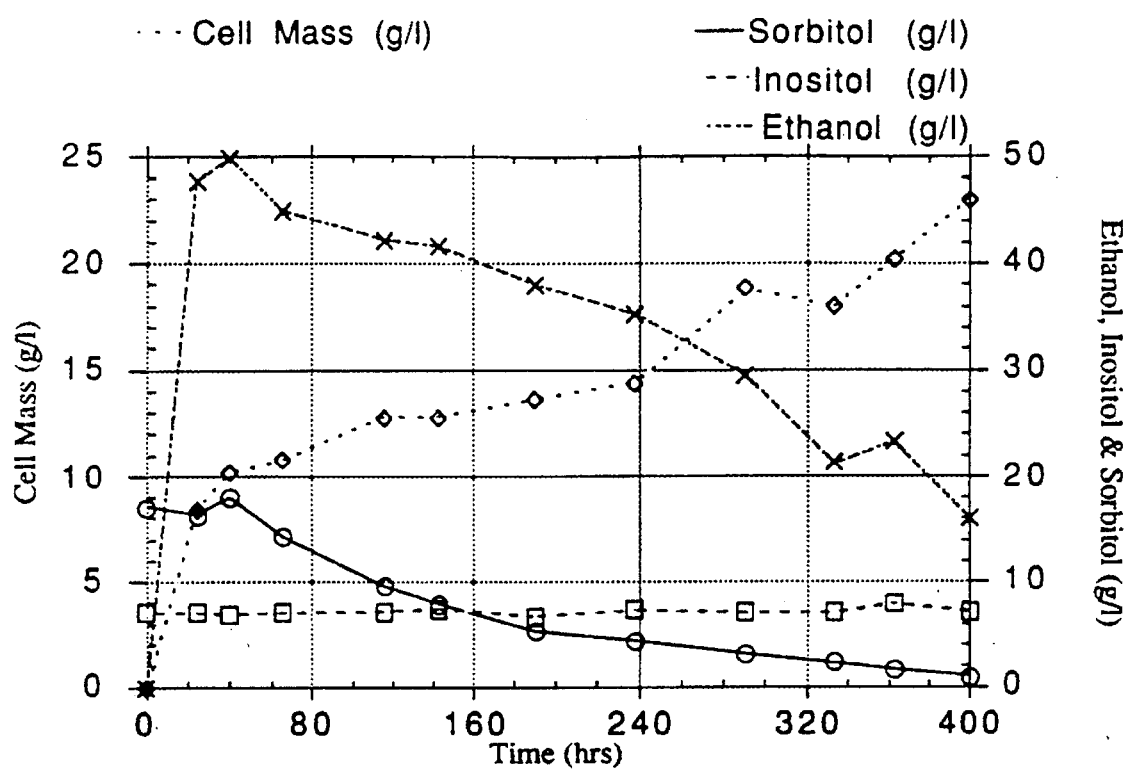
Figure 3 – Treatment of Unmodified 21° B AHJ with aDD2

METHOD OF PURIFYING CYCLITOLS

FIELD OF THE INVENTION

A method is described which allows simple separation of cyclitols and alditols from mono- and disaccharides. This is particularly useful in purifying cyclitols and alditol from plant sources, including corn steep liquor and almond hull juice.

BACKGROUND OF THE INVENTION

Cyclitols such as inositol are found in nature in a large number of plants. Inositol has been identified as a valuable nutrient and was for some time classified as one of the B-vitamins. Inositol was first claimed to have vitamin activity by D. W. Woolley, primarily due to its antialopecia effect in mice. M. J. Jackson, S. Shin, *Cold Spring Harbor Conf. Cell Proliferation,* 9, 75 (1982). Classification as a vitamin was however confused for some time due to difficulties in analytical techniques for inositol and the successive findings of great variability in endogenous synthesis of inositol in different animals and different tissue types within these animals.

Inositol is not now considered a true vitamin for humans, although it is clear that it is essential for the survival and growth of many human cell types. Animals, including humans, normally synthesize endogenous inositol, but inositol deficiency can exist in animals which can lead to disease conditions. B. J. Holub, *Ann. Rev. Nutr.,* 6, 563 (1986). Recognizing the importance of inositol in animals, especially during periods of rapid growth, the U.S. Food and Drug Administration has set a requirement for inclusion of inositol in infant formulas which do not contain milk (a good source of inositol). 21 C.F.R. §107.100 (1987).

In yeast, and possibly higher animals, inositol appears to play some essential role in membrane phospholipid balance, and is required for proper growth. See Greenberg et al., *Genetics,* 100:19–33 (Jan. 1982). The standard commercial source for inositol is corn steep liquor, since inositol is present as phytic acid in corn. See Artz, et al., U.S. Pat. No. 2,615,053, and The Merck Index, compound 4823, page 788, Merck & Co., 11th Ed. (1989).

Traditionally, inositol or cyclitols have been separated from a mixture of alditols and sugars, both simple and complex. Inositol has been purified by selective adsorption on zeolite molecular sieves. Chao, U.S. Pat. No. 4,482,761. Cyclitols can be crystallized from a mixture of sugars, but such crystallizations typically include and occlude a significant number of impurities. Another traditional method of purification is to pass a mixture of sugars, alditols and cyclitols through an appropriate column to separate cyclitols from other sugars before crystallization.

SUMMARY OF THE INVENTION

The present invention describes a method of selectively removing sugars from a mixture of sugars and sugar alcohols. The present invention also includes a method for removing alditols from the cyclitols, further simplifying purification of cyclitols. The feed stock for this invention can be any of a number of plant juices, including corn steep liquor, almond hull juice, cane and beet sugar molasses, sorghum molasses, wood molasses, and various fruit juices including cherry, plum (prone), pineapple, citrus, apple, etc.

*Saccharomyces cerevisiae* was used to consume sugars present in a nutrient medium. In a variation of the invention, a wild type strain of *S. cerevisiae* was adapted to preferentially consume sorbitol without consuming cyclitols. The resulting nutrient mixture was filtered and concentrated, then cyclitols were crystallized in high yield and high purity.

One object of this invention is to provide a solution of cyclitol relatively free of mono- or polysaccharides.

Another object of this invention is to provide highly purified, crystalline cyclitol.

BRIEF DESCRIPTION OF THE DRAWINGS

FIG. 1 illustrates the levels of various sugars and ethanol in a nutrient mixture of wild type *S. cerevisiae* growing on 30° Brix almond hull juice.

FIG. 2A illustrates the levels of various sugars and ethanol in a nutrient mixture of wild type *S. cerevisiae* growing on 12° Brix almond hull juice. FIG. 2B illustrates the levels of various sugars and ethanol in a nutrient mixture of wild type *S. cerevisiae* growing on 12° Brix almond hull juice, modified by addition of ammonium sulphate and potassium phosphate.

FIG. 3 illustrates the levels of various sugars and ethanol in a nutrient mixture of adapted *S. cerevisiae* growing on 21° Brix almond hull juice.

DETAILED DESCRIPTION

Inositol was separated from other carbohydrates in plant juice extracts. One suitable plant juice is almond hull juice, prepared by leaching almond hulls with hot water. A 30° Brix solution of almond hull juice (AHJ) has roughly 175.0 g/l of fermentable sugars, mostly glucose, fructose and sucrose. See Table 2, below. Other suitable plant juices include, for example, corn steep liquor, cane and beet sugar molasses, sorghum molasses, wood molasses, and various fruit juices including cherry, plum (prone), pineapple, citrus, apple, etc. Juices can be prepared by leaching the plant material using a suitable solvent, usually hot water. See W. L. McCabe and J. C. Smith, *Unit Operations of Chemical Engineering,* Third Edition, McGraw Hill, New York (1976). The specific leaching process and its operating conditions would in general depend on the plant material employed, as is well understood by persons skilled in the art.

The selected microorganism was used to ferment juice in a New Brunswick Scientific fermenter as described below. Samples were removed periodically for analysis. When analysis showed that inositol was essentially free of sugars, the mixture was filtered, solvent was partially removed, and inositol was crystallized. Mixtures of inositol and sorbitol could be selectively crystallized to provide both products in high purity.

As described in Example 1, the treatment of unmodified AHJ with the wild strain of *S. cerevisiae* (DD2) first led to the conversion of sugars into ethanol and cell mass (sugar utilization phase) followed by the consumption of ethanol to produce additional cell mass (ethanol utilization phase). At the end of the microbial treatment process, the fermentation broth contained the fermentation product cell mass and inositol and sorbitol originally present in AHJ. After this process, any further treatment with DD2 did not produce any noticeable change in the broth.

AHJ is rich in sugars—it contains necessary carbon substrates for growth. It also contains a significant quantity of the alditol sorbitol. Can microbial treatment with or without any modification of AHJ lead to removal of sugars as well as the alditol present in AHJ?

A technique, as described below in Example 3 was formulated to develop an adapted strain of *S. cerevisiae* termed 'aDD2' with the ability to consume sugars as well as alditols such as sorbitol and mannitol. Treatment of AHJ or any other similar solution with aDD2 can be expected to yield a fermentation broth free of sugars and alditols and containing cyclitols, originally present in the solution, as the only non-cellular product. Treatment of AHJ or any other similar solution with aDD2 will be desired over treatment with the wild strain DD2, if the removal of both sugars as well as alditols from the solution is essential for purification of the cyclitols left in the solution.

In broad terms, the mechanism of alditol metabolism by yeast has been elucidated. First alditols are oxidized to the corresponding aldose by means of a coenzyme linked dehydrogenase. The alditol dehydrogenase which catalyzes the reaction often has low specificity toward the alditol substrate. For this reason, a single such dehydrogenase may be responsible for the conversion of more than one alditol to its corresponding aldose. Barnett, J. A. in "The Fungi", 3, 557 (1968). Thus, if the strain of S. cerevisiae used can synthesize an alditol dehydrogenase, it may well be able to utilize sorbitol. Conversely, if it can grow in sorbitol, it would possibly consume other alditols, for example, mannitol.

Although the possible mechanistic pathway for sorbitol utilization by a yeast is known, the situation as to whether S. cerevisiae will grow on sorbitol is far from clear. In an early reference, it was claimed that S. cerevisiae is variable vis-a-vis growth on sorbitol. Morris, E. O. in "The Chemistry and Biology of Yeast", Ed. A. H. Cook, pp. 251–321, Academic Press, New York (1958). A more recent study dealing with the transport of alditols in S. cerevisiae concluded that sorbitol, like many other alditols, was not metabolized by S. cerevisiae. Canh D. S., Horak, J., Kotyk, A. and Rihova, L., Folia Microbiol., 20, 320–325 (1975). An isolated statement to the same effect has also been made by Barnett, loc. cit.

As described in Example 2, the strain DD2 of S. cerevisiae can simultaneously utilize ethanol and sorbitol in the presence of additional nitrogen and phosphorous sources in AHJ. Thus under appropriate conditions, DD2 can synthesize alditol dehydrogenase to metabolize sorbitol present in AHJ. Since alditol dehydrogenase enzyme is a non-specific enzyme, it follows that the strain could be adapted to produce a strain with the ability to metabolize sugars as well as alditols.

Crystallization Theory The crystallization process from a solution involves the initial nucleation of the material to be crystallized, its growth to this final size, or crystal size distribution, and recovery from solution. Since the first recorded sugar crystallizations from solution, ca. 500 A.D., efforts have been made to (1) control the nucleation step, which in turn leads to a narrower crystal size distribution, (2) improve product yield and (3) improve product purity. R. C. Bennett, Chem. Eng. Progress Symp. Series, 65(95), 34 (1969).

The chemical composition of the solution from which a compound is to be crystallized affects nucleation kinetics as well as crystal morphology ("shape"), which has significant practical and commercial implications. The chemical composition of the solution will also contribute to impurity problems of the crystal product either as crystal inclusion impurity or absorbed impurities on the crystal surface. The chemical composition of the solution will affect product yield either by decreasing the practical degree of supersaturation attainable prior to nucleation (cf: below), or by necessitating additional recrystallization steps to purify the product.

The first step in the crystallization process is reaching the optimum supersaturation point for the compound in solution. Inositol has a marked temperature dependent solubility. Crystallizing inositol from a solution of inositol in water should be, and is, a straightforward procedure of concentration of inositol in water at an elevated temperature, via evaporation, or some other means of water removal, followed by temperature reduction to initiate nucleation, with or without the introduction of "seed" crystals.

The sugar alcohol inositol, as found in almond hull juice extract, is in the presence of mono and disaccharides, namely glucose, fructose, sucrose, and sorbitol. The ratio of the sugars to inositol is approximately 8–10:1. Concentration of inositol in almond hull extract to the supersaturation point is best preceded by an inositol "enrichment" step: i.e. the concentration of inositol should be increased relative to the concentration of other sugars and sugar-like components. The method of the present invention provides a very favorable concentration ratio of inositol to other sugar components. This also can be accomplished for example via a "chromatographic" separation.

Concentrating inositol along with concentrating the other sugars would result in severe viscosity problems affecting nucleation and crystal growth, and potentially severe contamination of the inositol crystals by adsorption or inclusion of other sugars. Furthermore, yield per each batch crystallization step would be reduced due to viscosity and contaminant interference with achieving a high "$\Delta C$," where $\Delta C = C_{supersat.} - C_{sat.}$ i.e. the concentration of supersaturated inositol minus concentration of saturated inositol. This terminology is not equivalent to the accepted definition of supersaturation $P = C_{super} - C_{sat.}$ (constant temp)

which refers to the concentration of a material at supersaturation point, minus concentration at saturation point, at the same temperature. The "$\Delta C$" referred to above is meant to emphasize the high supersaturation of inositol which can be achieved by exploiting the temperature dependent concentration properties of inositol. Stated in another way, perhaps, inositol can be supersaturated into the labile supersaturated region, where seed nucleation is not necessary, rather than the metastable supersaturation region, where seeding is necessary for nucleation.

A procedure for enriching inositol from an almond hull extract, i.e., increasing inositol concentration relative to the other sugars, in a more economical manner than via a chromatographic step, is then seen to have significant industrial process advantages.

A procedure for converting compounds which are potential impurities and/or crystallization inhibitors to compounds which enhance growth and yield, would represent an even more dramatic improvement in the crystallization of inositol from solution. Conversion of the other sugars to ethanol while leaving inositol intact represents one such procedure. Crystallization of inositol from water-alcohol solution avoids contamination by other sugars, aids nucleation (alcohol "precipitation" of sugars and sugar alcohols from aqueous solutions is a well known chemical procedure), and increases yield per batch crystallization, both by immediate mass production and by reduction of subsequent recrystallization steps. Additionally, crystallization of inositol from water-ethanol solution eliminates the necessity for initiating nucleation of inositol crystals above 50 degrees centigrade. That necessity is imposed if anhydrous inositol crystals (the inositol crystal form in present commerce) are desired, rather than inositol dihydrate crystals.

Crystallization Method Inositol was crystallized from the filtered biological reactions, yielding anhydrous inositol crystals of greater than 90% purity in the initial crystallization. Recrystallization gave a product of over 99% purity.

Materials and Methods

Microorganisms: The wild strain of S. cerevisiae can be easily obtained from American Type Culture Collection (ATCC). Other strains of S. cerevisiae with desired properties, such as fermentation characteristics, can be obtained from commercial suppliers such as ATCC. Two strains of S. cerevisiae were used in this study, including wild type diploid strain of S. cerevisiae designated DD2 in our laboratory. An adaptation study was conducted with this wild type strain of S. cerevisiae in nutrient media containing predominantly alditols to produce an adapted strain of S. cerevisiae, aDD2, possessing the ability to consume alditols as well as sugars present in a nutrient medium.

Nutrient Media: Several nutrient media were used in this experimental study. Table 2 gives the composition of the synthetic nutrient medium used. The other nutrient medium used was AHJ with or without any modifications as discussed in the examples below. The nutrient media were filter sterilized using a pre-sterilized 0.20 micron rated filter cartridge.

TABLE 1

A Typical Synthetic Liquid Medium Composition for Baker's Yeast

| Component | Medium Concentration |
|---|---|
| MINERALS | |
| 1) $(NH)_4SO_4$ | 10.00 g/l |
| 2) $KH_2PO_4$ | 2.50 g/l |
| 3) $MgSO_4.7H_2O$ | 1.00 g/l |
| 4) $CaCl_2.2H_2O$ | 0.70 g/l |
| 5) NaCl | 0.50 g/l |
| 6) $FeSO_4.7H_2O$ | 40.00 mg/l |
| 7) $MnSO_4.H_2O$ | 20.00 mg/l |
| 8) $ZnSO_4.7H_2O$ | 15.00 mg/l |
| 9) $CuSO_4.5H_2O$ | 4.00 mg/l |
| 10) $H_3BO_3$ | 100.00 µg/l |
| 11) $MoO_3$ | 50.00 µg/l |
| 12) $CoCl_3.6H_2O$ | 50.00 µg/l |
| 13) $NiSO_4.6H_2O$ | 50.00 µg/l |
| 14) KI | 50.00 µg/l |
| VITAMINS AND PRECURSORS | |
| 15) Inositol | 100.00 mg/l |
| 16) Thiamine-HCl | 100.00 mg/l |
| 17) Calcium Pantothenate | 50.00 mg/l |
| 18) Pyridoxine-HCl | 25.00 mg/l |
| 19) d-Biotin | 0.25 mg/l |
| CARBON & ENERGY SOURCE | |
| Glucose | 50.00 g/l |

Experimental System: A two liter New Brunswick Scientific fermenter, with operating volume of one liter, interfaced to a Digital MICRO/PDP-11 microcomputer system was used in this work. The temperature of fermentation broth in all the experiments was controlled at 30° C. Mixing in the fermenter was provided by a set of three disk turbine impellers. Agitation speed was controlled at a constant value which ranged between 200 to 600 rpm. Filter sterilized air was passed through the fermenter at a rate equal to 1.0 slpm per liter of the culture broth (unless otherwise specified) using a mass flow controller and the microcomputer.

The pH of the fermenter broth was digitally controlled at 5.50 by addition of either 2N NaOH or 2N NH4OH.

Cell Dry Weight and Elemental Analysis: The cell dry weight was determined by dispensing 25 ml of culture into a dried and preweighed centrifuge tube. The tube was centrifuged at 10,000 rpm for 15 minutes. The supernatant was carefully poured off. The cell pellet was resuspended in 15 ml of a 0.5 g/l NaCl solution. The tube was centrifuged again at 10,000 rpm for 15 minutes. The second supernatant was poured off. The centrifuge tube containing the washed cell pellet was dried at 95° C. for 24 hours. The tube was finally weighed to yield the 95° C. weight of the dry pellet. The cell dry weight was then calculated based on the volume of the culture sample and correlated with the measure of the optical density of the culture measured at 600 nm.

Residual Carbohydrate Composition: Culture samples were immediately filtered through a 0.2 micron membrane. The carbohydrate composition in culture filtrates was determined using a Beckman Model 132 HPLC system equipped with a Beckman Model 110B pump, a refractive index detector and a carbohydrate column.

Residual Ethanol Concentration: The culture filtrate were also analyzed for ethanol contents by using a Hewlett Packard Model 5890A gas chromatograph equipped with an F.I.D. detector and a Porapak Q column.

EXAMPLES

Example 1

Treatment of AHJ with the Wild Strain of S. cerevisiae

A 30° Brix solution of almond hull juice (AHJ) has roughly 175.0 g/l of fermentable sugars, mostly glucose, fructose and sucrose. Several fermentation experiments were conducted with the DD2 wild strain of S. cerevisiae in unmodified AHJ solution. A typical set of results describing the fermentation of a 30° Brix solution of AHJ with the strain DD2 is presented in Table 2 and FIG. 1.

The growth of DD2 in AHJ occurred in two distinct phases:

Sugar Utilization Phase (0–30 hours): In this phase, the microorganisms rapidly consumed all the sugars present in AHJ to produce ethanol, cell mass and $CO_2$. At the end of this phase the fermentation broth contained two fermentation products, namely, cell mass (13.1 g/l) and ethanol (54.4 g/l) and two other major components, namely sorbitol (21.8 g/l) and inositol (10.1 g/l), which were as originally present in AHJ.

At the end of the sugar utilization phase of some experiments, the microorganisms were separated from the fermentation broth to yield a cell-free liquor. The cell-free liquor was concentrated and inositol was separated by crystallization. Moreover, ethanol as well as sorbitol were recovered as additional products from the spent liquor.

TABLE 2

| Time | Sugars | Glucose | Fructose | Sucrose | Sorbitol | Inositol | Cell Mass | Ethanol |
|---|---|---|---|---|---|---|---|---|
| 0 | 175.7 | 97.3 | 72.3 | 6.1 | 21.4 | 10.1 | 0.7 | 0 |
| 10.2 | 165.3 | 89.9 | 69.2 | 6.2 | 21.7 | 10.1 | 1.2 | 5.1 |
| 17.2 | 153.1 | 79.2 | 68.5 | 5.4 | 22 | 10.1 | 3.9 | 17.9 |
| 20.6 | 117.7 | 51 | 61.1 | 5.5 | 21.8 | 10.1 | 7 | 28.9 |

TABLE 2-continued

| Time | Sugars | Glucose | Fructose | Sucrose | Sorbitol | Inositol | Cell Mass | Ethanol |
|---|---|---|---|---|---|---|---|---|
| 27.2 | 14.8 | 1.7 | 10 | 3.1 | 22 | 10.1 | 11.7 | 49.4 |
| 30.3 | 7.2 | 0 | 4.9 | 2.3 | 21.8 | 10.1 | 13.1 | 54.4 |
| 33.2 | 0 | 0 | 0 | 0 | 22 | 10.1 | 13.1 | 50 |
| 40.5 | 0 | 0 | 0 | 0 | 21.8 | 10.1 | 13.7 | 35.7 |
| 57.5 | 0 | 0 | 0 | 0 | 21.8 | 10.1 | 15.3 | 23.1 |
| 73.7 | 0 | 0 | 0 | 0 | 21.8 | 10.1 | 17 | 13.9 |
| 92.4 | 0 | 0 | 0 | 0 | 21.8 | 10.1 | 18.4 | 6.5 |
| 127.7 | 0 | 0 | 0 | 0 | 21.8 | 10.1 | 20.9 | 3.7 |
| 146.5 | 0 | 0 | 0 | 0 | 21.8 | 10.1 | 23.5 | 0 |

Time in hours, all other values grams/liter

Ethanol Utilization Phase (30–150 hours): In other experiments, the microbial treatment was continued after the sugar utilization phase, during which the microorganisms consumed ethanol from the fermentation broth to produce additional cell mass and $CO_2$ (FIGS. 1A and 1B).

The ethanol utilization phase will be of importance if it is desired to convert ethanol to produce cellular protein mass as the sole fermentation product. After the ethanol utilization phase in one experiment, the cell mass was removed from the fermentation broth to yield a solution containing inositol (10.1 g/l) and sorbitol (21.8 g/l)—the cyclitol and the alditol originally present in AHJ. The cell-free liquor was sufficiently concentrated to allow separation of inositol by crystallization. The sorbitol remaining in the spent liquor can also be recovered as an additional product if so desired.

Example 2

Treatment of Modified AHJ with the Wild Strain of *S. cerevisiae*

The nitrogen content of yeast cells is about 10% of dry weight, thus it is an important component of yeast, and essential for continued production of new protoplasm. Yeast generally obtain this element from simple substances such as ammonium salts, nitrates, amino acids, amides and urea. In general, ammonium sulfate is the most widely used nitrogen source in industrial fermentations, with 70–400 mg/l being added to black strap fermentation such as molasses. See Undrkofler, L. Z. and Hickey, R. J., (Eds.) in "Industrial Fermentations", v. 1, p. 17, Chemical Publishing Co., New York, 1954; Paturau, J. M. in "By-products of the Cane Sugar Industry", p. 171, Elsevier, Amsterdam, 1969; and Rose, A. H. and Harrison, J. S., (Eds.) in "The Yeasts", v.3, p. 306, Academic Press, London, 1970. Ammonium sulfate is generally preferred to urea since it also provides a readily assimilable source of sulfur. Many complex sources of nitrogen, such as mixtures of amino acids, nucleic acids, simple bases, fatty acids, peptides and lipid materials, etc., also have been shown to enhance growth and fermentation in yeast. Since AHJ supports vigorous growth of DD2 on sugars (Example 1), it is possible that AHJ contains some of these complex sources of nitrogen.

An elemental analysis of the non-volatile matter in AHJ was conducted to yield the following results:

% C=38.86; % H=7.76; % N=0.60; % P=0.19 and % 0 (estimated) =51.81

Examination of the above results clearly indicate the fact that AHJ is little lean in nitrogen and phosphorous. Thus AHJ solutions were modified by adding various quantities of nitrogen and phosphorous containing salts. The modified AHJ solutions were then subjected to the microbial treatment using the wild strain of *S. cerevisiae* (DD2).

TABLE 3A

| Time | Sugars | Glucose | Fructose | Sucrose | Sorbitol | Inositol | Cell Mass | Ethanol |
|---|---|---|---|---|---|---|---|---|
| 0 | 71 | 40.4 | 26.4 | 4.2 | 13.5 | 5.3 | 0 | 0 |
| 38 | 0 | 0 | 0 | 0 | 13.5 | 5.3 | 7.9 | 24.9 |
| 85.5 | 0 | 0 | 0 | 0 | 12.8 | 5.2 | 9 | 19.31 |
| 154.4 | 0 | 0 | 0 | 0 | 13 | 5.1 | 9.6 | 14.7 |
| 188 | 0 | 0 | 0 | 0 | 13 | 5.3 | 10.1 | 10.2 |
| 257.5 | 0 | 0 | 0 | 0 | 13.2 | 5.1 | 10.6 | 3.4 |
| 311.5 | 0 | 0 | 0 | 0 | 14 | 5.1 | 10.8 | 0.06 |
| 518 | 0 | 0 | 0 | 0 | 14 | 5.1 | 11.6 | 0 |

Time in hours, all other values grams/liter

TABLE 3B

| Time | Sugars | Glucose | Fructose | Sucrose | Sorbitol | Inositol | Cell Mass | Ethanol |
|---|---|---|---|---|---|---|---|---|
| 0 | 71 | 40.4 | 26.4 | 4.2 | 13.5 | 5.3 | 0 | 0 |
| 38 | 0 | 0 | 0 | 0 | 13.5 | 5.3 | 8.8 | 23.9 |
| 85.5 | 0 | 0 | 0 | 0 | 12.5 | 6 | 9.7 | 19.2 |
| 188 | 0 | 0 | 0 | 0 | 3.2 | 6.6 | 13.4 | 14.5 |
| 282 | 0 | 0 | 0 | 0 | 1 | 6.6 | 16.2 | 7.4 |
| 447 | 0 | 0 | 0 | 0 | 1.1 | 7.1 | 18 | 0 |

Time in hours, all other values grams/liter

A typical set of experimental results are presented in Tables 3A and 3B and FIGS. 2A and 2B. In this set of experiments, two media were used, an unmodified 12° Brix AHJ solution (FIG. 2A), and a 12° Brix AHJ solution modified by addition of 16 g/l of $(NH_4)_2SO_4$ and 4 g/l of $KH_2PO_4$ (FIG. 2B). In the second medium, the ammonium sulfate served as an additional inorganic nitrogen source while the potassium phosphate was added as a phosphorous source. In each of the two media, the sugars—sucrose, glucose and fructose—were completely utilized in less than 24 hours with ethanol reaching its maximum concentration at the end of the sugar utilization phase. However, as illustrated by FIGS. 2A and 2B, the behavior of DD2 differed dramatically in the two media. In the case of AHJ occurred in less than 24 hours followed by production of about 50.0 g/l of ethanol in the culture medium. After the sugar utilization phase, the microorganisms began to metabolize sorbitol as well as ethanol from the fermentation broth. After nearly 400 hours, the microorganisms could metabolize sorbitol while leaving roughly 16.0 g/l of ethanol in the medium. At this stage, it is possible to separate cells from the broth to yield a liquor containing the cyclitol inositol free from sugars as well as the alditol sorbitol. The liquor can be sufficiently concentrated to separate out inositol by crystallization.

TABLE 4

| Time | Sugars | Glucose | Fructose | Sucrose | Sorbitol | Inositol | Cell Mass | Ethanol |
|------|--------|---------|----------|---------|----------|----------|-----------|---------|
| 0    | 89.9   | 51.2    | 33.4     | 5.3     | 17.1     | 7.1      | 0         | 0       |
| 24   | 0      | 0       | 0        | 0       | 16.4     | 7.1      | 8.4       | 47.6    |
| 40   | 0      | 0       | 0        | 0       | 18       | 7        | 10.2      | 49.9    |
| 65   | 0      | 0       | 0        | 0       | 14.3     | 7.1      | 10.8      | 45      |
| 115  | 0      | 0       | 0        | 0       | 9.7      | 7.2      | 12.8      | 42.2    |
| 143  | 0      | 0       | 0        | 0       | 7.9      | 7.4      | 12.8      | 41.6    |
| 190  | 0      | 0       | 0        | 0       | 5.4      | 6.7      | 13.6      | 38      |
| 238  | 0      | 0       | 0        | 0       | 4.4      | 7.3      | 14.4      | 35.2    |
| 291  | 0      | 0       | 0        | 0       | 3.1      | 7.1      | 18.8      | 29.4    |
| 333  | 0      | 0       | 0        | 0       | 2.3      | 7.1      | 18        | 21.2    |
| 362  | 0      | 0       | 0        | 0       | 1.7      | 7.9      | 20.2      | 23.3    |
| 400  | 0      | 0       | 0        | 0       | 1        | 7.2      | 23        | 16.1    |

Time in hours, all other values grams/liter unmodified AHJ, the sugar utilization phase was followed by the ethanol utilization phase with no noticeable changes in concentrations of sorbitol and inositol. In the case of modified AHJ, however, concomitant consumption of ethanol and sorbitol occurred in the second phase of growth with only a little change in the concentration of inositol in the medium. The final cell mass concentration in the modified AHJ was higher than in the unmodified AHJ suggesting that in the presence of inorganic nitrogen and phosphorous DD2 can metabolize sorbitol in addition to sugars and ethanol to form additional cell mass.

Example 3

Cultivation of the Wild Strain of *S. cerevisiae* in Sorbitol to Yield an Adapted Strain of *S. cerevisiae*

An adapted strain of *S. cerevisiae*, termed as aDD2, was developed by taking cells from a culture of DD2 in modified AHJ from which sorbitol was metabolized and further cultivating them repeatedly on agar plates containing 2% bactopeptone, 1% yeast extract, 2% agar and 2% sorbitol. Single colonies from such plates were used to develop cultures in synthetic media containing sorbitol as the sole source of the carbon nutrient. Development of cultures in such synthetic medium ensured the adaptation of original strain DD2 to form the strain aDD2 possessing the ability to metabolize sugars as well as alditols.

Treatment of Unmodified AHJ with the Adapted Strain of *S. cerevisiae*

Unlike the strain DD2, the adapted strain aDD2 of *S. cerevisiae* is found to be able to metabolize sorbitol in unmodified AHJ. A typical set of experimental results illustrating this characteristic feature of the strain aDD2 is presented in Table 4 and FIG. 3. A complete utilization of approximately 90.0 g/l of sugars in a 21° Brix solution of

What is claimed is:

1. A method of purifying cyclitols comprising:
   preparing a plant extract mixture containing at least one cyclitol and other carbohydrates;
   adding to said plant extract mixture a microorganism which consumes an alditol; and
   substantially reducing the concentration of an alditol in the plant extract mixture, whereby the concentration of said cyclitol or cyclitols is enhanced relative to the concentration of said alditol.

2. The method of claim 1, wherein said plant extract mixture comprises inositol.

3. The method of claim 1 wherein said plant extract mixture contains one principal cyclitol and that cyclitol is inositol.

4. The method of claim 1 wherein said plant extract mixture comprises almond hull juice.

5. The method of claim 1 wherein said microorganism is *Saccharomyces cerevisiae*.

6. The method of claim 1 wherein said microorganism is the DD2 strain of *Saccharomyces cerevisiae*.

7. The method of claim 1 wherein said plant extract mixture is modified almond hull juice.

8. The method of claim 1 wherein said plant extract includes sorbitol.

9. The method of claim 1 wherein said microorganism consumes sorbitol.

10. The method of claim 1 wherein said microorganism is aDD2, the DD2 strain of *Saccharomyces cerevisiae*, adapted to preferentially metabolize sorbitol.

11. The method of claim 1 wherein said plant extract mixture is selected from the group consisting of corn steep liquor, almond hull juice, cane and beet sugar molasses, sorghum molasses, wood molasses, cherry, plum, prone, pineapple, citrus, and apple juices.

* * * * *